US011096595B2

(12) United States Patent
Albadawi et al.

(10) Patent No.: US 11,096,595 B2
(45) Date of Patent: Aug. 24, 2021

(54) BLOOD PRESSURE DETERMINATIONS

(71) Applicant: Microsoft Technology Licensing, LLC, Redmond, WA (US)

(72) Inventors: Haithem Albadawi, Redmond, WA (US); Zongyi Liu, Redmond, WA (US); Christopher Nuesmeyer, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 555 days.

(21) Appl. No.: 15/351,934

(22) Filed: Nov. 15, 2016

(65) Prior Publication Data

US 2018/0132731 A1 May 17, 2018

(51) Int. Cl.
*A61B 5/021* (2006.01)
*A61B 5/026* (2006.01)
(Continued)

(52) U.S. Cl.
CPC ............ *A61B 5/021* (2013.01); *A61B 5/0077* (2013.01); *A61B 5/0261* (2013.01); *A61B 5/349* (2021.01);
(Continued)

(58) Field of Classification Search
CPC ..... A61B 5/021; A61B 5/0261; A61B 5/0452; A61B 5/681; A61B 5/7267; A61B 5/0077;
(Continued)

(56) References Cited

U.S. PATENT DOCUMENTS 6,527,725 B1   3/2003  Inukai et al.
9,161,700 B2  10/2015  Banet et al.
(Continued)

FOREIGN PATENT DOCUMENTS

CN    102429649 B    2/2014
CN    105105734 A   12/2015
(Continued)

OTHER PUBLICATIONS

"International Search Report and Written Opinion Issued in PCT Application No. PCT/US2017/060484", dated Feb. 27, 2018, 13 Pages.
(Continued)

*Primary Examiner* — Hien N Nguyen
(74) *Attorney, Agent, or Firm* — Arent Fox LLP

(57) ABSTRACT

Methods and devices for blood pressure monitoring may include receiving one or more sensor measurements from the at least one sensor. The methods and devices may further include determining at least one of a first blood pressure indication using a first regression representation based on the one or more sensor measurements, a second blood pressure indication using a second regression representation based on the one or more sensor measurements, or a third blood pressure indication using a third regression representation based on the one or more sensor measurements. The methods and devices may include performing a blood pressure selection procedure using the first blood pressure indication, the second blood pressure indication, and the third blood pressure indication to determine an estimated blood pressure indication based on one or more classification characteristics. The methods and devices may further include transmitting the estimated blood pressure indication to the output device.

20 Claims, 9 Drawing Sheets

(51) Int. Cl.
  *A61B 5/00*   (2006.01)
  *A61B 5/349*  (2021.01)
  *A61B 5/352*  (2021.01)
  *A61B 5/11*   (2006.01)
  *A61B 5/024*  (2006.01)

(52) U.S. Cl.
  CPC .............. *A61B 5/352* (2021.01); *A61B 5/681* (2013.01); *A61B 5/7267* (2013.01); *A61B 5/742* (2013.01); *A61B 5/02108* (2013.01); *A61B 5/02416* (2013.01); *A61B 5/1123* (2013.01); *A61B 2562/0219* (2013.01)

(58) Field of Classification Search
  CPC ................. A61B 5/0456; A61B 5/742; A61B 2562/0219; A61B 5/1123; A61B 5/02108; A61B 5/02416
  See application file for complete search history.

(56) References Cited

U.S. PATENT DOCUMENTS

| | | | |
|---|---|---|---|
| 2006/0074322 | A1 | 4/2006 | Nitzan |
| 2008/0214942 | A1 | 9/2008 | Oh et al. |
| 2011/0245690 | A1* | 10/2011 | Watson .................. A61B 5/022 600/485 |
| 2015/0031965 | A1* | 1/2015 | Visvanathan ........ A61B 5/0059 600/301 |
| 2015/0305675 | A1 | 10/2015 | Miller et al. |
| 2016/0166160 | A1 | 6/2016 | Casale |
| 2017/0181649 | A1 | 6/2017 | Carter et al. |
| 2018/0199893 | A1* | 7/2018 | Hubner ................ A61B 5/7282 |

FOREIGN PATENT DOCUMENTS

| | | |
|---|---|---|
| EP | 3033991 A1 | 6/2016 |
| EP | 3061391 A1 | 8/2016 |
| WO | 2011110491 A1 | 9/2011 |

OTHER PUBLICATIONS

Kim, et al., "Comparative study on artificial neural network with multiple regressions for continuous estimation of blood pressure", In Proceedings of IEEE 27th Annual Conference on Engineering in Medicine and Biology, Sep. 1, 2005, pp. 6942-6945.

Wang, et al., "Cuff-Free Blood Pressure Estimation Using Pulse Transit Time and Heart Rate", In Journal of International Conference of Signal Processing, Oct. 2014, pp. 1-12.

Sheng, et al., "A wireless wearable body sensor network for continuous noninvasive blood pressure monitoring using multiple parameters", In Proceedings of the 2nd international conference on Circuits, Systems, Communications & Computers, Dec. 10, 2011, pp. 308-314.

Lee, et al., "Measurement of Blood Pressure Using an Arterial Pulsimeter Equipped with a Hall Device", In Journal of Sensors, vol. 11, Issue 2, Jan. 31, 2011, pp. 1784-1793.

Thomas, et al., "BioWatch: A Noninvasive Wrist-Based Blood Pressure Monitor That Incorporates Training Techniques for Posture and Subject Variability", In IEEE Journal of Biomedical and Health Informatics, vol. 20, Issue 5, Sep. 2016, pp. 1291-1300.

Thomas, et al., "Demonstration abstract: BioWatch: a wrist watch based physiological signal acquisition system", In Proceedings of the 13th international symposium on Information processing in sensor networks, Apr. 15, 2014, pp. 349-350.

Waldin, Alexander, "Learning Blood Pressure Behavior from Large Blood Pressure Waveform Repositories and Building Predictive Models", In Master Thesis of MIT, Jun. 10, 2013, 60 pages.

Thomas, et al., "BioWatch—A Wrist Watch based Signal Acquisition System for Physiological Signals including Blood Pressure", In Proceedings of 36th Annual International Conference of the IEEE Engineering in Medicine and Biology Society, Aug. 26, 2014, pp. 2286-2289.

\* cited by examiner

BLOOD PRESSURE DETERMINATIONS

BACKGROUND

The present disclosure relate to electronic devices, and more particularly, to blood pressure determinations using a wearable electronic device.

Use of computing devices is becoming more ubiquitous by the day. Computing devices range from standard desktop computers to wearable computing technology and beyond. The field of wearable devices has grown in recent years with the introduction of fitness bands and smart watches, some of which can interface with a nearby mobile device via short range communication technology (e.g., Bluetooth) to provide information thereto and/or to obtain and display information therefrom for consumption by a user wearing the fitness band or smart watch. These devices may include GPS systems, altimeters, and stopwatches, for example, and may track a user's speed, position and time while running, bicycling, skiing, etc. One problem with such devices is that they typically do not present the user with accurate information other than time and position information. As such, users may connect conventional external sensors, such as non-invasive blood pressure devices to obtain biometric feedback. However, the use of multiple components in this manner may be bulky and make performance of various activities such as exercise awkward.

Thus, there is a need in the art for improvements in blood pressure monitoring using a wearable electronic device.

SUMMARY

The following presents a simplified summary of one or more implementations in order to provide a basic understanding of such implementations. This summary is not an extensive overview of all contemplated implementations, and is intended to neither identify key or critical elements of all implementations nor delineate the scope of any or all implementations. Its purpose is to present some concepts of one or more implementations in a simplified form as a prelude to the more detailed description that is presented later.

In one example, a method of blood pressure monitoring is provided. In particular, the method may include receiving one or more sensor measurements from at least one sensor. The method may further include determining at least one of a first blood pressure indication using a first regression representation based on the one or more sensor measurements, a second blood pressure indication using a second regression representation based on the one or more sensor measurements, or a third blood pressure indication using a third regression representation based on the one or more sensor measurements. Additionally, the method may include performing a blood pressure selection procedure using at least one of the first blood pressure indication, the second blood pressure indication, or the third blood pressure indication to determine an estimated blood pressure indication based on one or more classification characteristics. Moreover, the method includes transmitting the estimated blood pressure indication to an output device.

In another example, an electronic device comprising a memory to store data and instructions, at least one sensor to obtain one or more sensor measurements, and a processor in communication with the memory and the at least one sensor may monitor blood pressure. The processor may be configured to receive one or more sensor measurements from the at least one sensor. The processor may further be configured to determine at least one of a first blood pressure indication using a first regression representation based on the one or more sensor measurements, a second blood pressure indication using a second regression representation based on the one or more sensor measurements, or a third blood pressure indication using a third regression representation based on the one or more sensor measurements. Additionally, the processor may be configured to perform a blood pressure selection procedure using at least one of the first blood pressure indication, the second blood pressure indication, or the third blood pressure indication to determine an estimated blood pressure indication based on one or more classification characteristics. Moreover, the processor may be configured to transmit the estimated blood pressure indication to an output device.

In a further example, a computer-readable medium storing instructions executable by an electronic device may monitor blood pressure. The computer-readable medium may include at least one instruction for causing the computer device to receive one or more sensor measurements from at least one sensor. The computer-readable medium may further include at least one instruction for determine at least one of a first blood pressure indication using a first regression representation based on the one or more sensor measurements, a second blood pressure indication using a second regression representation based on the one or more sensor measurements, or a third blood pressure indication using a third regression representation based on the one or more sensor measurements. Additionally, the computer-readable medium may include at least one instruction for perform a blood pressure selection procedure using at least one of the first blood pressure indication, the second blood pressure indication, or the third blood pressure indication to determine an estimated blood pressure indication based on one or more classification characteristics. Moreover, the computer-readable medium may include at least one instruction for transmit the estimated blood pressure indication to an output device.

Additional advantages and novel features relating to implementations of the present disclosure will be set forth in part in the description that follows, and in part will become more apparent to those skilled in the art upon examination of the following or upon learning by practice thereof.

DESCRIPTION OF THE FIGURES

The specific features, implementations, and advantages of the disclosure will become better understood with regard to the following description, appended claims, and accompanying drawings where:

DETAILED DESCRIPTION

Figure 1A:
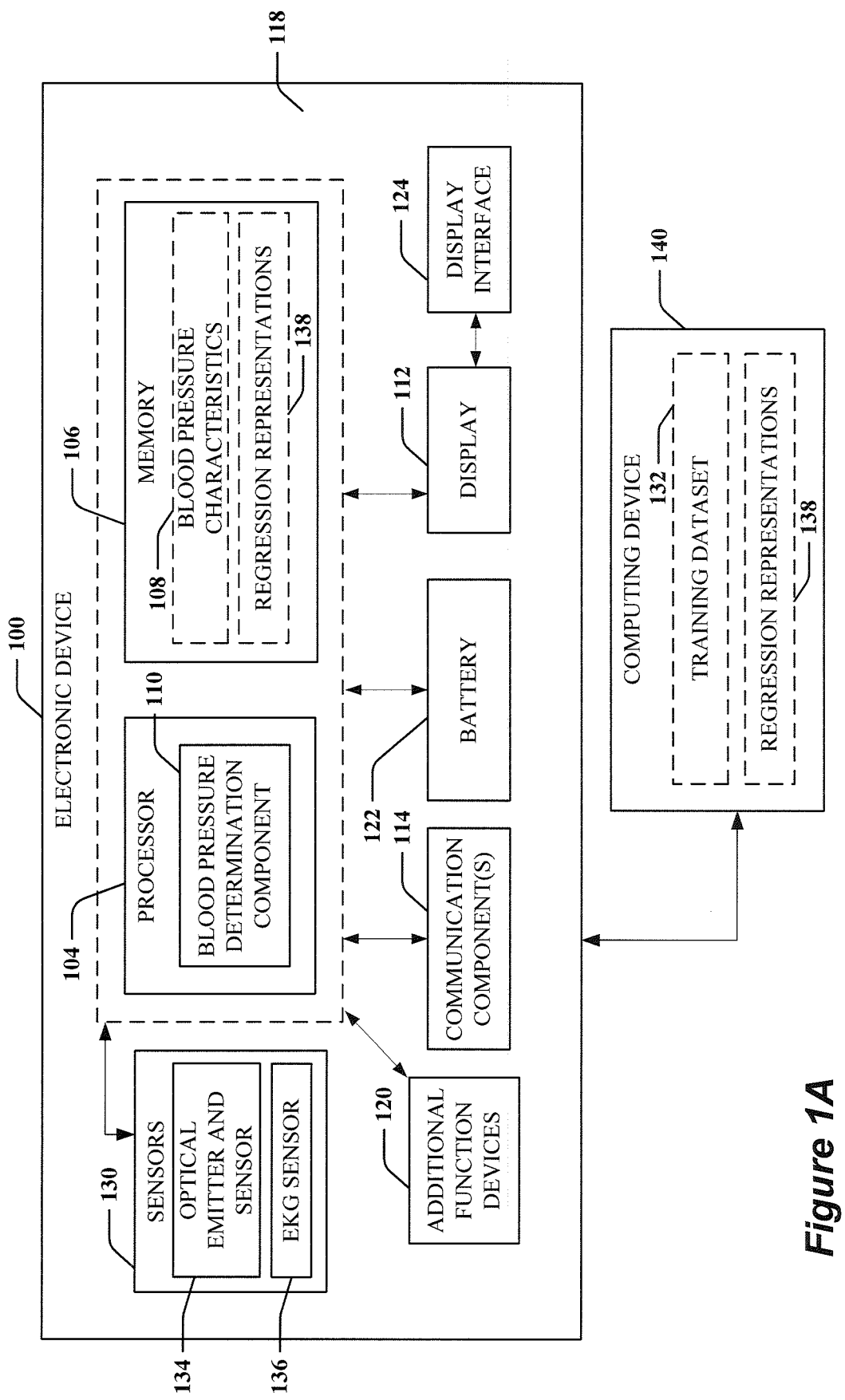
FIG. 1A is a schematic block diagram of an example electronic device including a blood pressure determination component that may be in communication with a computing device in accordance with some implementations.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts. In some implementations, examples may be depicted with reference to one or more components and one or more methods that may perform the actions or operations described herein, where components and/or actions/operations in dashed line may be optional.

The present disclosure relates to systolic blood pressure estimation using multiple regression models at a wearable electronic device. Detecting systolic blood pressure using a wearable electronic device may be challenging using conventional blood pressure machines employing a cuff and pressure sensors. Indeed, the cumbersome approach to determining blood pressure using such bulky equipment defeats the purpose of a small and integrated wearable electronic device. As such, in some implementations, blood pressure may be estimated based on one or more biometric measurements utilizing one or more sensors in the wearable electronic device. Such biometric measurements may include an electrocardiogram (EKG) measurement and/or a photoplethysmography (PPG) measurement. In some implementations, an EKG measurement or signal may provide a recording or indication of the electrical activity of a heart over a period of time. Further, in some implementations, a PPG measurement or signal may provide an indication of a heart rate based on a reflection of light through a user's capillaries.

Additionally, in some implementations, pulse transit time (PTT), which is the time it takes a pulse wave to travel between two arterial sites, may be used in conjunction with EKG and PPG measurements to correlate blood pressure using a single blood pressure regression model (e.g., statistical process for estimating the relationships among variables). Although PTT may provide a useful representation of blood pressure for a portion of the general population (e.g., a portion of users using a wearable electronic device), the use of PTT (e.g., in conjunction with EKG and PPG) in formulating an estimated blood pressure based on a single regression model for the general population may not provide an accurate representation of blood pressure for each individual.

That is, metrics such as PTT may not correlate with blood pressure over time, thus rendering a single regression model based on PTT inaccurate. For example, the PTT time may not only be affected by the blood pressure, but also by many other variables, such as body composition, stress level, strength of the heartbeat, weight, etc. Further, the correlation between PTT and the systolic blood pressure may be low (e.g., ~0.15) when the population size or sample grows large (e.g., >100 subjects). Additionally, even for the same person, the PTT and the systolic blood pressure may not correlate accurately if they are sampled at large intervals (e.g., sampled days apart). Accordingly, a single blood pressure regression model utilizing, among other metrics, PTT, may not provide an accurate representation of blood pressure.

As such, the present implementations provide a multifaceted approach for blood pressure determinations that utilize at least three regression models. Specifically, one or more measurements including an EKG measurement and a PPG measurement may be acquired by the electronic device. Subsequently, one or more blood pressure features or characteristics may be extracted or determined based on the EKG measurement and the PPG measurement. The blood pressure features or characteristics may be unique for the point in time corresponding to when the measurement took place. That is, such features or characteristics may change or otherwise be dynamic based on a user's activity level. Moreover, each of the at least three regression models may utilize the blood pressure features or characteristics to provide a corresponding blood pressure value indicating a particular blood pressure class in which the user belongs and a likelihood or probability associated with each blood pressure value. The wearable electronic device may then determine an estimated blood pressure based on the blood pressure values and corresponding likelihood or probability associated with each blood pressure value.

Figure 1B:
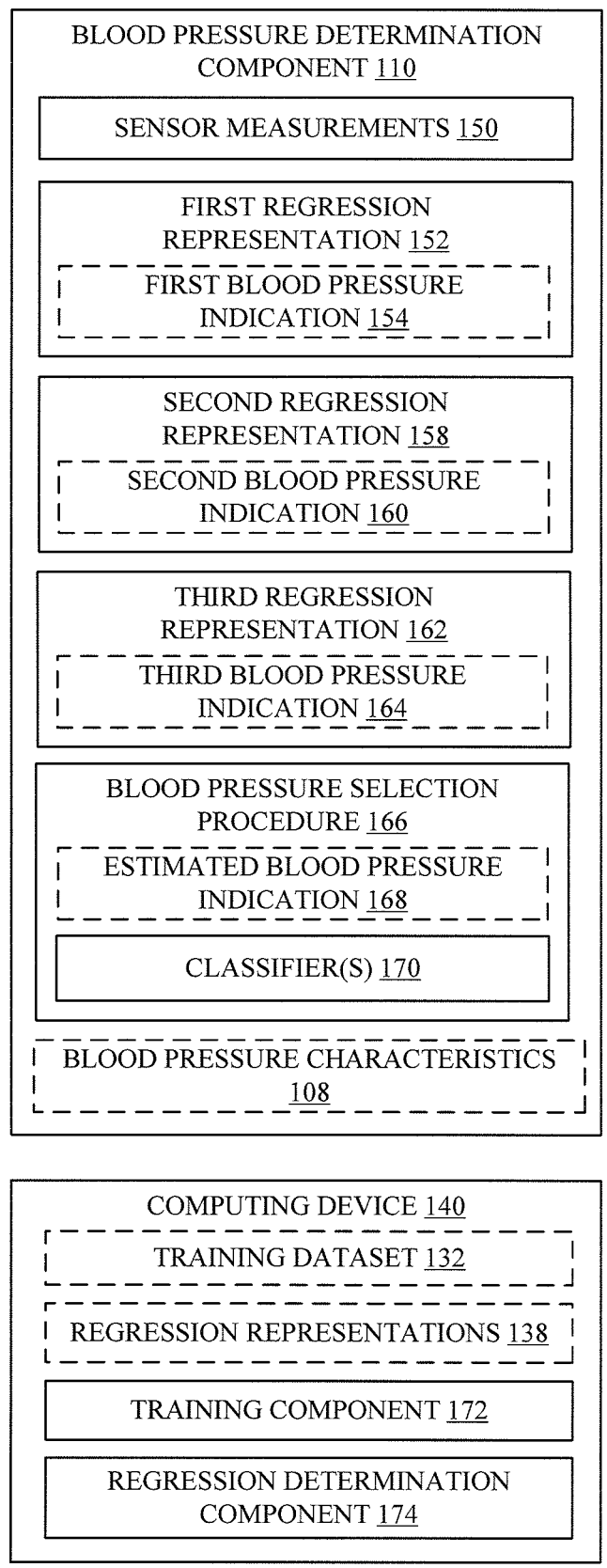
FIG. 1B is a schematic block diagram of the blood pressure determination component and various subcomponents in accordance with some implementations.

Referring now to FIGS. 1A and 1B, an example electronic device 100 may include one or more components and/or subcomponents such as a blood pressure determination component 110 for determining a blood pressure of a user of the electronic device 100. In some implementations, electronic device 100 may be or otherwise take the form of a smart watch, fitness band, and/or other wearable device. In some implementations, electronic device 100 may include or may otherwise be coupled with a processor 104 and/or memory 106, where the processor 104 and/or memory 106 may be configured to execute or store instructions or other parameters, such as blood pressure parameters 108, related to executing a blood pressure determination component 110 for determining a blood pressure of a user of the electronic device 100. For example, blood pressure determination component 110 can correspond to one or more of an operating system of the electronic device 100 (e.g., a mobile operating system), or an application executing on the operating system of the electronic device 100.

In some implementations, electronic device 100 may also include a display 112 having a presentation area, such as a screen, for presenting one or more graphical interfaces (e.g., graphical user interfaces (GUI)), such as to provide information for consumption by a user wearing the electronic device 100. For example, the display 112 may be or may include a liquid crystal display (LCD), light emitting diode (LED), organic LED (OLED), high-contrast electronic ink (E-Ink), a fabric including light pipes, or micro-LED array, and may display graphical interfaces as instructed by processor 104 (e.g., based on execution of the blood pressure determination component 110). Electronic device 100 may also include a display interface 124 that couples to display 112 to provide instructions, parameters, etc. for displaying the graphical interfaces. In some implementations, the display 112 and/or the display interface 124 may form a touch-sensitive display that may detect touch inputs on the display 112 (e.g., for interacting with a user interface) and also output data in the form of graphical representations (e.g., on user interface).

Further, in some implementations, electronic device 100 may also include one or more communication component(s) 114 for communicating with a computing device 140 via a wired or wireless interface (Bluetooth, radio frequency identification (RFID), near field communication (NFC), etc.). Electronic device 100 may also include a battery 122 for providing power to various components and/or subcomponents of the electronic device 100.

In some implementations, electronic device 100 may also include one or more sensors 130, which may include an optical emitter and sensor 134 for transmitting and detecting light to and from a capillary of a user of the electronic device. The light signals/indications may be used to determine a PPG signal/indication corresponding to a heart rate of the user. Further, the one or more sensors 130 may also include an EKG sensor 136 in the form of an electrical pulse/signal sensor. For example, the EKG sensor 136 may detect an electrical signal/indication corresponding to an EKG signal based on detecting contact of at least a finger of each hand of a user with the electronic device 100.

In some implementations, the one or more sensors 130 may also include an accelerometer for detecting at least acceleration of the electronic device 100, a gyro sensor for detecting angular velocity of the electronic device 100, an angle or orientation sensor for detecting a position of electronic device 100 relative to a reference plan, a compass for determining a direction of magnetic north and bearing from it, an ultraviolet (UV) sensor for detecting light in the ultraviolet spectrum, and/or a barometer for measuring atmospheric pressure.

In addition, electronic device 100 may include one or more additional function devices 120 for providing additional functionality to the modular device core 100, such as a global positioning system (GPS) radio, a fitness tracking device (step tracking device, pulse monitor or tracking device, power meter, etc.), a battery, a microphone, a galvanic skin sensor, a memory, a processor, communication interface, such as a RFID radio, Bluetooth radio, Wi-Fi radio, etc.

In some implementations, electronic device 100 (and/or computer device 140) may include an operating system executed by processor 104 and/or memory 106 of electronic device 100. Memory 106 may be configured for storing data and/or computer-executable instructions defining and/or associated with operating system (and/or firmware), and processor 104 may execute operating system and/or one or more associated components such as blood pressure determination component 110. An example of memory 106 can include, but is not limited to, a type of memory usable by a computer, such as random access memory (RAM), read only memory (ROM), tapes, magnetic discs, optical discs, volatile memory, non-volatile memory, and any combination thereof. An example of processor 104 may include, but is not limited to, any processor specially programmed as described herein, including a controller, microcontroller, application specific integrated circuit (ASIC), field programmable gate array (FPGA), system on chip (SoC), or other programmable logic or state machine.

Specifically, in some implementations, computing device 140, which may be remote from the electronic device 100, may be configured to receive a training dataset 132 including one or both of PPG and EKG data. The computing device 140 may be configured to determine, using regression determination component 174, the one or more regression representations 138 (e.g., first regression representation 152, second regression representation 158, and/or third regression representation 162) based at least on, for example, the training dataset 132.

For example, the computing device 140 may sample at least a subset of the training dataset 132 to determine or otherwise construct a single regression representation (or model). In some implementations, the computing device 140 may sample the entire training dataset 132. The computing device 140 may then be configured to divide or split the subset of the training dataset into three subsets, each of which may be of equal or unequal size. Using the three subsets of the training dataset 132, the computing device 140, via regression determination component 174, may determine a regression representation (or model) for each of the three subsets (e.g., to obtain first regression representation 152, second regression representation 158, and/or third regression representation 162). Further, computing device 140 may adjust, via regression determination component 174, each of the regression representations 138 based on moving the subsets of the training dataset 132 across the regression representations 138 in order to improve the correlation coefficients.

Additionally, the computing device 140 may be configured to train, via training component 172, at least two systolic blood pressure range classifiers 170, which may include a first blood pressure classifier that indicates a high systolic blood pressure (e.g., >=135 millimeter of mercury (mmHg)), and a second blood pressure classifier that indicates a low systolic blood pressure (e.g., <105 mmHg). For the first blood pressure classifier, the computing device 140 may sample a first subset of measurements from the training dataset 132, a portion of which may each have a blood pressure value greater than or equal to a first threshold value (e.g., >=135 mmHg) and a second portion of which may each have a blood pressure value less than a second threshold value (e.g., <130 mmHg).

The computing device 140 may be configured to determine the first blood pressure classifier based on performing a support vector machine (SVM) (e.g., with each individual SVM being a linear SVM that builds a model for assigning users to a blood pressure category) and a bag tree (e.g., decision tree ensemble trained using aggregation) on the sampled subsets using the one or more blood pressure parameters 108, which may include body mass index (BMI), gender, PPG based area ratio and normalized maximum gradient value, and EKG based average HR, QR and/or RS pulse segment lengths. The computing device 140 may also use the first blood pressure classifier to predict other measurements in the training dataset 132, and for those misclassified, the training component 172 may use the measurements in further tuning the first blood pressure classifier until the data and the first blood pressure classifier converge.

Further, in determining the second blood pressure classifier, the computing device 140 may perform a similar procedure as described above with respect to determining the first blood pressure classifier yet using a second subset of measurements from the training dataset 132 differing from the first subset used in determining the first blood pressure classifier. For example, the second subset may include a first portion each having a blood pressure value greater than or equal to a first threshold value (e.g., >=110 mmHg) and a second portion of which each may have a blood pressure value less than a second threshold value (e.g., <=105 mmHg). The portions may be of the same or different sizes. Additionally, the threshold values used in determining the first and second blood pressure classifiers may each be distinct.

In some implementations, the computing device 140 may include or otherwise correspond to any mobile or fixed computer device, which may be connectable to a network. The computing device 140 may be, for example, a desktop or laptop or tablet computer, a cellular telephone, a personal digital assistant (PDA), or a handheld device, or any other computer device having wired and/or wireless connection capability with one or more other devices. The computing device 140 may also include one or more components similar to the electronic device 100 such as, but not limited to, at least one processor and a memory. The computing device 140 may be configured to transmit at least the regression representations 138 (e.g., first regression representation 152, second regression representation 158, and/or third regression representation 162) to the electronic device 100 via a wired or wireless connection.

Using the regression representations 138 provided by the computing device 140, the electronic device 100 may be configured to determine an estimated (systolic) blood pressure indication 169 of a user of the electronic device 100 via the blood pressure determination component 110. Specifically, the blood pressure determination component 110 may be configured to determine at least three blood pressure indications, and intelligently combine them into one value using the prediction results of the blood pressure classifiers 170.

For example, the blood pressure determination component 110 may be configured to receive one or more sensor measurements 150, which may include an EKG measurement from the EKG sensor 136 and/or a PPG measurement from the optical emitter and sensor 134. The blood pressure determination component 110 may be configured to determine one or more blood pressure characteristics 108 for determining the blood pressure indications, as well as for performing the blood pressure selection procedure 166. The blood pressure characteristics 108 may include, but are not limited to an EKG RS wave segment characteristic that is based on the EKG measurement, and/or a PPG area ratio value that is based on the PPG measurement. In some implementations, an RS wave segment includes the electrical characteristics between the R wave (e.g., first upward wave deflection after the P wave) and the S wave (e.g., first downward deflection occurring after the R wave). The blood pressure characteristics 108 may further include, but are not limited to an average heartrate for a defined time duration that is based on one or both of the PPG measurement or the EKG measurement, an EKG QR width characteristic and an EKG RS width characteristic that are based on the EKG measurement, a normalized maximum gradient value of the PPG measurement, and/or a PPG area ratio value that is based on the PPG measurement. In some implementations, a QR width may be a time value/duration between a Q wave (e.g., first downward deflection after the P wave) and the R wave.

The blood pressure determination component 110 may be configured to determine at least one of a first blood pressure indication 154 using a first regression representation 152 based on at least one of the EKG RS wave segment characteristic or the PPG area ratio value, a second blood pressure indication 160 using a second regression representation 158 based on at least one of the EKG RS wave segment characteristic or the PPG area ratio value, and/or a third blood pressure indication 162 using a third regression representation 164 based on at least one of the EKG RS wave segment characteristic or the PPG area ratio value. In some implementations, the first blood pressure indication 154, the second blood pressure indication 164, the third blood pressure indication 164, and/or the estimated blood pressure indication 168 may be or otherwise correspond to a systolic blood pressure value in millimeters of mercury (mmHg).

As part of determining each of the blood pressure indications, blood pressure determination component 110 may also determine a probability value associated with each blood pressure indication that indicates a likelihood that the user belongs to or is associated with a distinct blood pressure class associated with a range of blood pressure values. The blood pressure determination component 110 may then be configured to perform a blood pressure selection procedure 166 using at least one of the first blood pressure indication 154, the second blood pressure indication 160, or the third blood pressure indication 164 to determine an estimated blood pressure indication 168 based on one or both of the classifiers 170 and/or at least one of the average heartrate for the defined time duration, the EKG QR width characteristic and the EKG RS width characteristic, the normalized maximum gradient value, or the PPG area ratio value.

In some implementations, in performing the blood pressure selection procedure, the blood pressure determination component 110 may be configured to average the first blood pressure indication 154, the second blood pressure indication 160, and the third blood pressure indication 164 to form the estimated blood pressure indication 168. That is, each regression model or representation may be assigned a weight that may be dependent on or correlated with the probability value of each blood pressure indication. Accordingly, the blood pressure determination component 110 may be configured to determine a weighted average of the first blood pressure indication 154, the second blood pressure indication 160, and the third blood pressure indication 164.

In some implementations, in performing the blood pressure selection procedure 166, the blood pressure determination component 110 may be configured to select one of the first blood pressure indication 154, the second blood pressure indication 160, or the third blood pressure indication 164 having a highest probability value. Further, blood pressure determination component 110 may be configured to provide the estimated (systolic) blood pressure indication 168 to the display 112 for presentation to the user.

Figure 2:
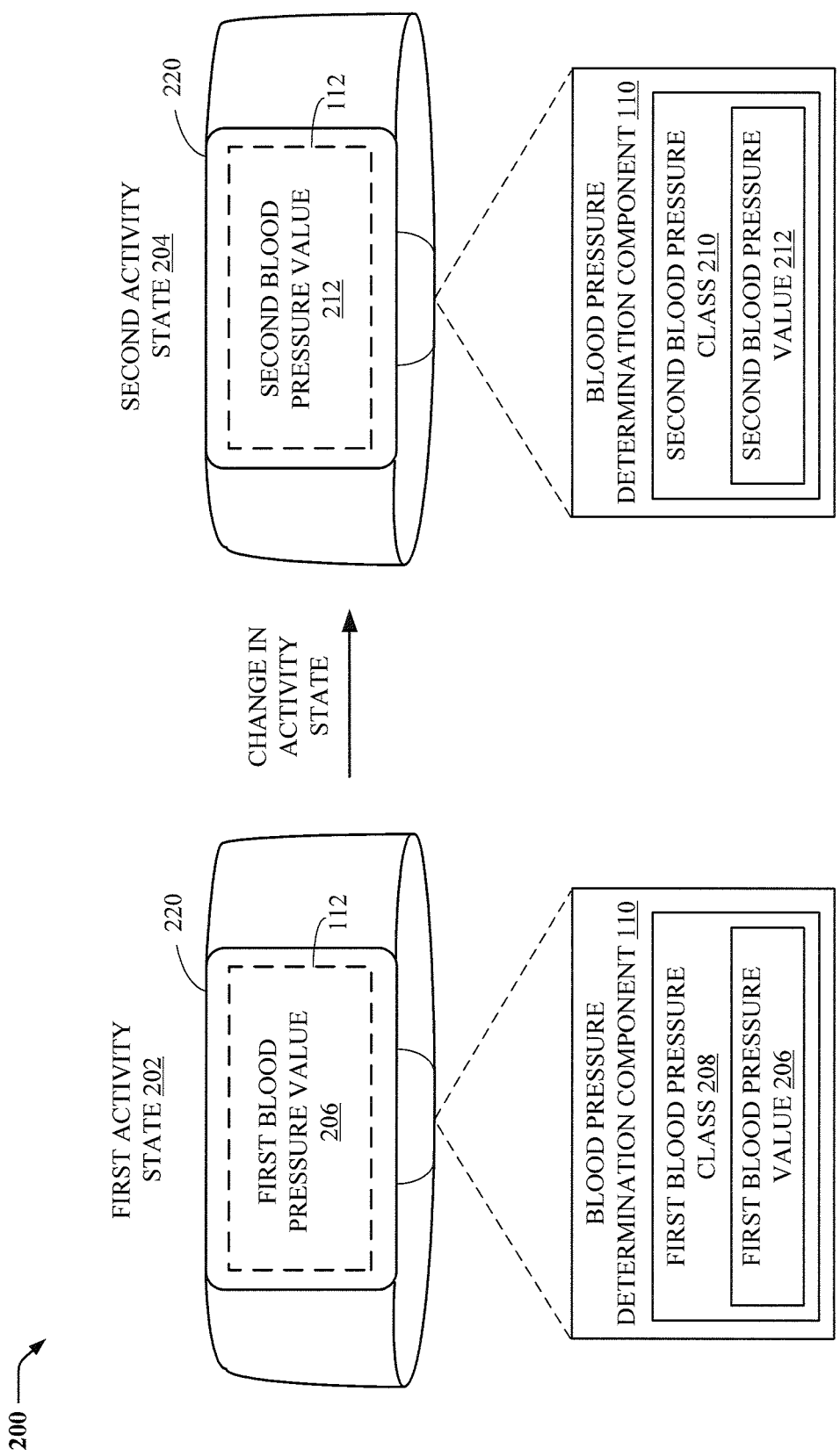
FIG. 2 is a conceptual diagram of blood pressure determinations at an example wearable electronic device in accordance with some implementations.

Referring now to FIG. 2, a conceptual diagram 200 of an example wearable electronic device 220 displaying blood pressure values in accordance with some implementations is shown. The conceptual diagram 200 illustrates the capability of the electronic device 220 to determine and display two distinct blood pressure values based on a change in an activity state of the user as detected by the wearable electronic device 220 within, for example, a short period of time. That is, the class structure associated with the regression models/representations permits a dynamic approach to blood pressure determinations. In some implementations, the wearable electronic device 220 may be the same as or similar to electronic device 100 (FIG. 1A). For example, during a blood pressure determination procedure, the wearable electronic device 220 may be in or otherwise detect a first activity state 202. The first activity state 202 may correspond to or otherwise include sitting, walking, running, etc.

The blood pressure determination component 110 may determine a first blood pressure value 206 during the first activity state 202 based on, for instance, at least the implementations described herein with respect to FIGS. 1A and 1B. Specifically, the blood pressure determination component 110 may determine, based on the one or more sensor measurements 150 (FIG. 1B) taken during the first activity state 202, that the user is associated with a first blood pressure class 208 having the first blood pressure value 206. The wearable electronic device 220 may display the first blood pressure value 206 (e.g., which may be a systolic value) on the display 112. A change in activity state may subsequently occur within a period of time. In particular, a user of the wearable electronic device 220 may enter into a second activity state, which may correspond to or otherwise include an activity that is distinct from the first activity state 202 (e.g., sitting, walking, running). The blood pressure determination component 110 may determine, based on the one or more sensor measurements 150 taken during the second activity state 204, that the user of the wearable electronic device 220 is now associated with or belongs to a second blood pressure class having a second blood pressure value. The wearable electronic device 220 may then display the second blood pressure value 212 (e.g., which may be a systolic value) on the display 112.

Figure 3:
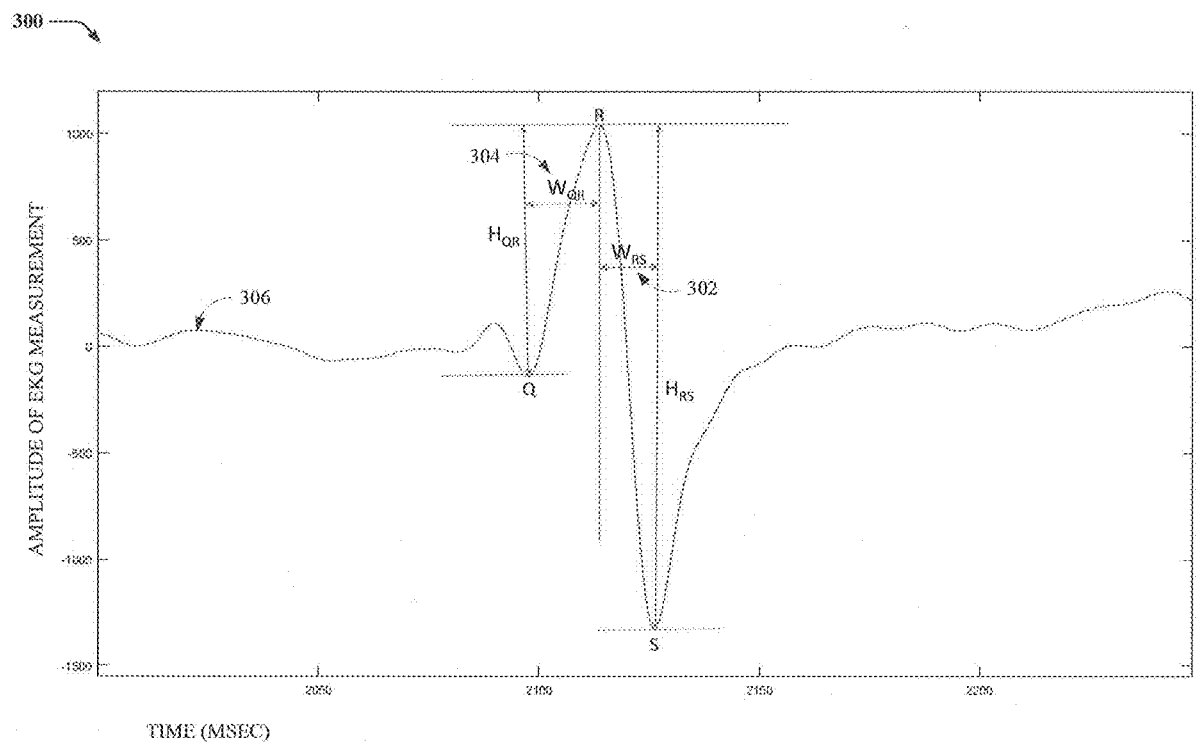
FIG. 3 is a graphical representation of an example electrocardiogram (EKG) measurement in accordance with some implementations.

FIG. 3 is a graphical representation 300 of an example EKG measurement 306 in an amplitude of the EKG measurement over time (in milliseconds) in accordance with some implementations. In some implementations, various features and/or characteristics of the EKG measurement 300 may be extracted and used as part of detecting blood pressure by the blood pressure determination component 110 (FIGS. 1A and 1B). For example, the EKG measurement 300 may be taken during an activity state of a user of the electronic device 100 (FIG. 1A). The EKG measurement 300 may include a number of waves and segments, such as, but not limited to, an 'RS' segment 302 and a 'QR' segment 304. In some implementations, as part of determining the blood pressure indications using the corresponding blood pressure regression representations, the blood pressure determination component 110 may utilize the 'RS' 302 segment indicating a width (e.g., in time) between the peak 'R' wave and the valley 'S' wave. Further, in some implementations, as part of performing the blood pressure selection procedure 166 (FIG. 1B), the blood pressure determination component 110 may base a group classification of a user on at least the 'QR' 304 width, which may be indicative of a width of the 'Q' wave and the peak 'R' wave, as well as the 'RS' 302 width.

Figure 4:
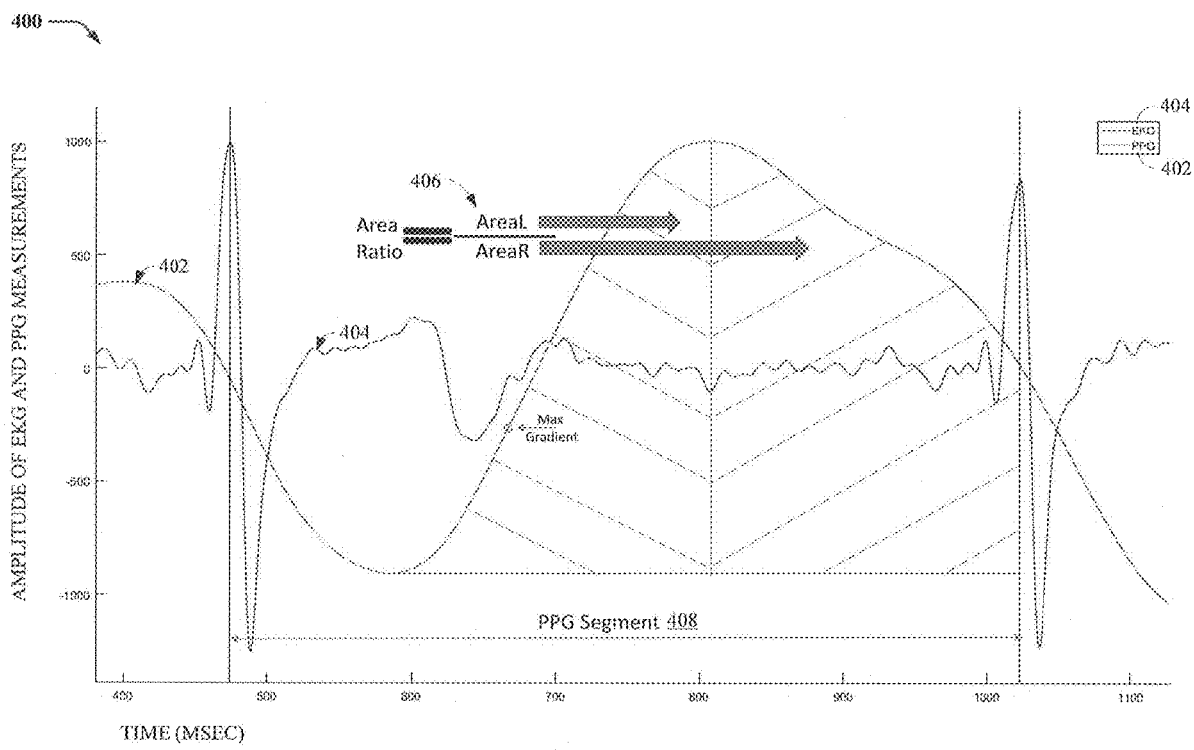
FIG. 4 is a graphical representation of an example photoplethysmography (PPG) measurement in accordance with some implementations.

FIG. 4 is a graphical representation 400 of an example PPG measurement 402 and an EKG measurement 404 in an amplitude of the EKG and PPG measurements over time (in milliseconds) in accordance with some implementations. In some implementations, various features and/or characteristics of the PPG measurement 402 may be extracted and used as part of detecting blood pressure by the blood pressure determination component 110 (FIGS. 1A and 1B). For example, the PPG measurement 402 may be taken during an activity state of a user of the electronic device 100 (FIG. 1A). Specifically, as part of determining the blood pressure indications using the corresponding blood pressure regression representations, and/or performing the blood pressure selection procedure 166 (FIG. 1B), the blood pressure determination component 110 may utilize a PPG area ratio 406 of a PPG segment 408, where an AreaL may be an area under curve from a previous minimum to a peak and an AreaR may be an area under curve from the peak to a next minimum. In some implementations, the PPG segment 408 may be indicative of a time between a first and second EKG 'R' wave.

Figure 5:
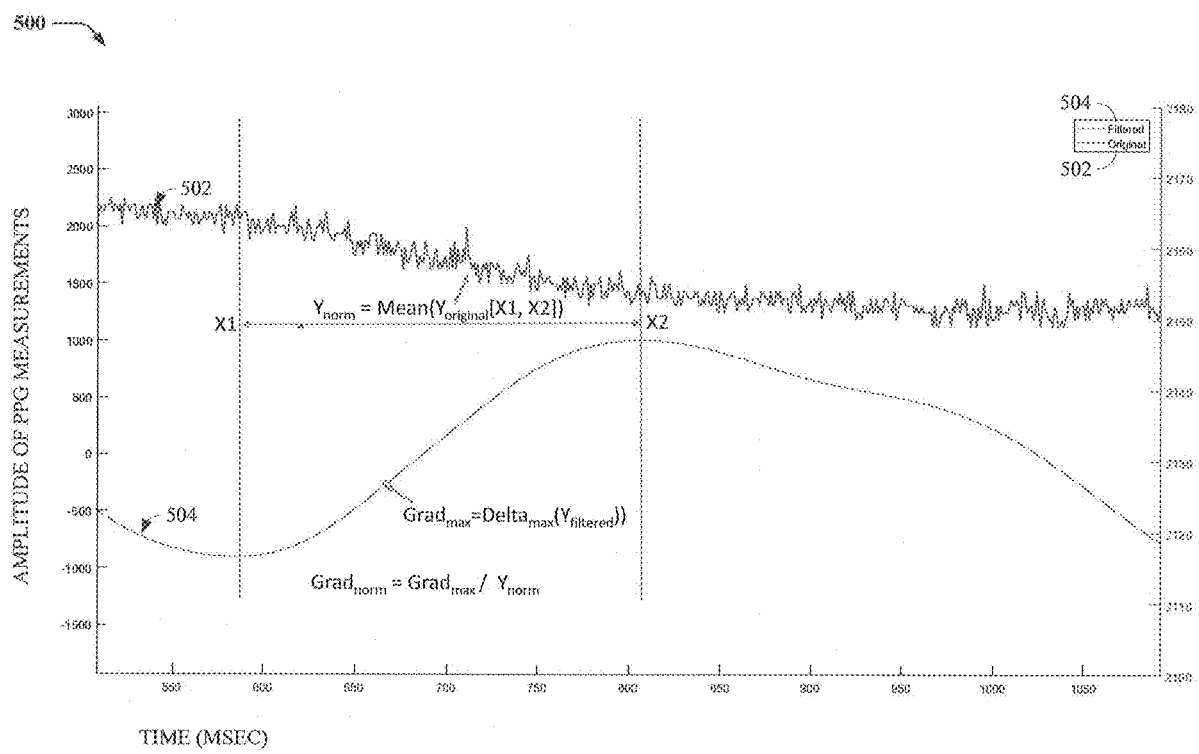
FIG. 5 is another graphical representation of an example PPG measurement in accordance with some implementations.

FIG. 5 is another graphical representation 500 of example PPG measurements including an original PPG measurement 502 and a filtered PPG measurement 504 in amplitude of PPG measurement over time (in milliseconds) in accordance with some implementations. Various features and/or characteristics of the PPG measurements may be extracted and used as part of detecting blood pressure by the blood pressure determination component 110 (FIGS. 1A and 1B). For example, the PPG measurements may be taken during an activity state of a user of the electronic device 100 (FIG. 1A). Specifically, as part of determining the blood pressure indications using the corresponding blood pressure regression representations, and/or performing the blood pressure selection procedure 166 (FIG. 1B), the blood pressure determination component 110 may utilize a normalized maximum gradient in filtered PPG measurement 504. In particular, the blood pressure determination component 110 may be configured to determine: $Y_{norm}=\text{Mean}(Y_{original}[X1, X2])$, where the normalized original PPG measurement 502)(norm represents the average of the original PPG measurement 502 between a first time X1 and a second time X2.

The blood pressure determination component 110 may also be configured to determine: $\text{Grad}_{max}=\text{Delta}_{max}(Y_{filtered})$, where the maximum gradient $\text{Grad}_{max}$ represents a maximum difference of a function of the filtered PPG measurement 504.

The blood pressure determination component 110 may be further configured to determine: $\text{Grad}_{norm}=\text{Grad}_{max}/Y_{norm}$, where the normalized maximum gradient $\text{Grad}_{norm}$ is equivalent to the maximum gradient divided by the normalized original PPG measurement 502 $Y_{norm}$.

Figure 6A:
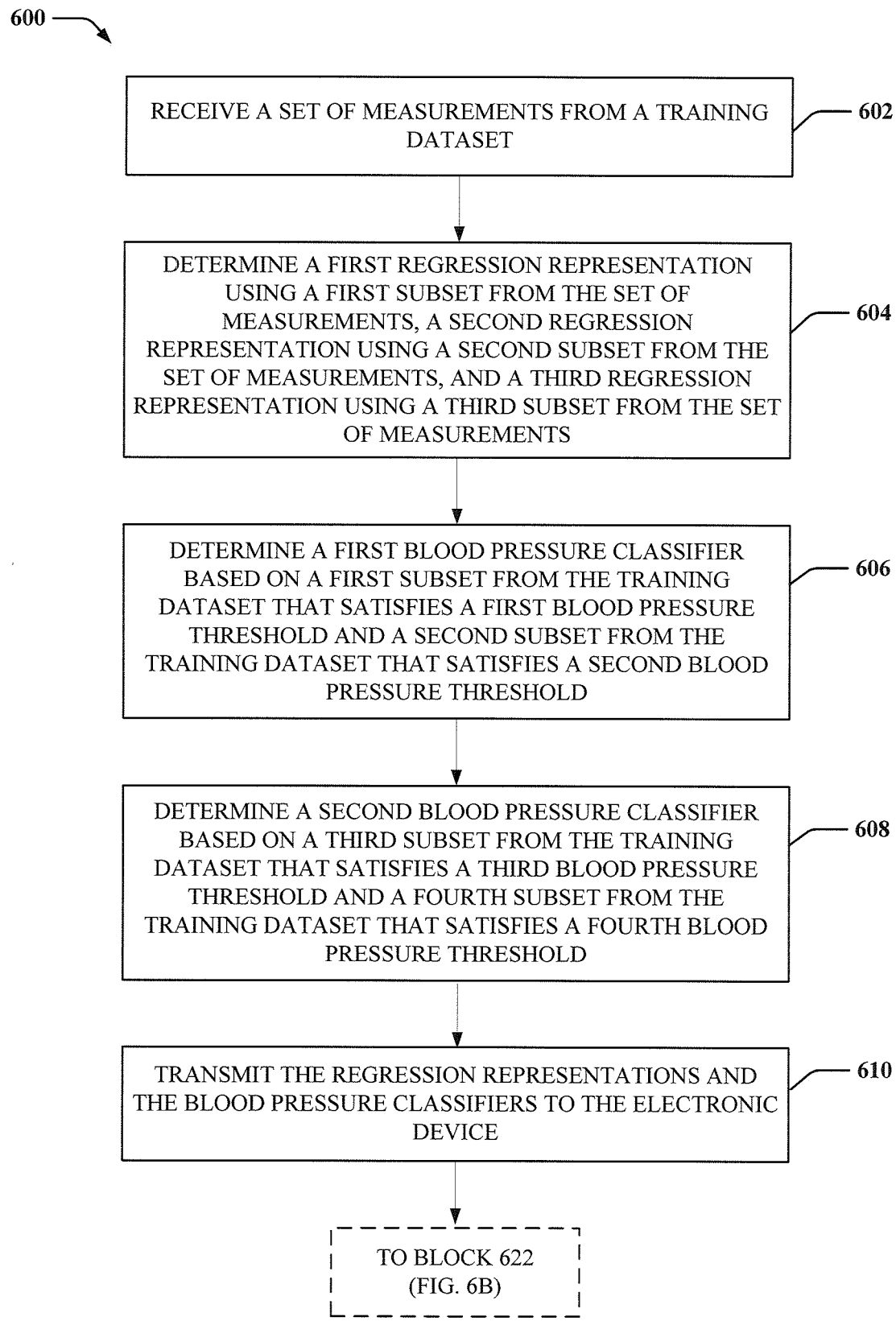
FIG. 6A is a flow chart of an example of a method of blood pressure regression determination in accordance with some implementations.

FIG. 6A is a flow diagram of an example of a method 600 related to regression representation determinations in accordance with various implementations of the present disclosure. Although the operations described below are presented in a particular order and/or as being performed by an example component, it should be understood that the ordering of the actions and the components performing the actions may be varied, depending on the implementation.

At block 602, method 600 may receive a set of measurements from a training dataset. In some implementations, computing device 140 (FIGS. 1A and 1B) may include a communications component to receive a set of measurements from a training dataset 132 (FIG. 1B).

Further, at block 604, method 600 may determine a first regression representation using a first subset from the set of measurements, a second regression representation using a second subset from the set of measurements, and a third regression representation using a third subset from the set of measurements. In some implementations, computing device 140 (FIGS. 1A and 1B) may execute regression determination component 174 (FIG. 1B) to determine a first regression representation 152 (FIG. 1B) using a first subset from the set of measurements, a second regression representation 160 (FIG. 1B) using a second subset from the set of measurements, and a third regression representation 162 (FIG. 1B) using a third subset from the set of measurements. In some implementations, the first, second, and third subsets may be of the same or distinct sizes. Further, in some implementations, each regression representation may determine a corresponding blood pressure indication associated with a particular blood pressure class and a probability value indicative of a likelihood that the user belongs to the particular blood pressure class.

At block 606, method 600 may determine a first blood pressure classifier based on a first subset from the training dataset that satisfies a first blood pressure threshold and a second subset from the training dataset that satisfies a second blood pressure threshold.

In some implementations, computing device 140 (FIGS. 1A and 1B) may execute training component 172 (FIG. 1B) to determine a first blood pressure classifier (e.g., as part of the classifiers 170, FIG. 1B) based on a first subset from the training dataset 132 (FIG. 1B) that satisfies a first blood pressure threshold and a second subset from the training dataset 132 that satisfies a second blood pressure threshold. In some implementations, the first blood pressure threshold and the second blood pressure threshold may be distinct blood pressure values.

At block 608, method 600 may determine a second blood pressure classifier based on a third subset from the training dataset that satisfies a third blood pressure threshold and a fourth subset from the training dataset that satisfies a fourth blood pressure threshold. In some implementations, computing device 140 (FIGS. 1A and 1B) may execute training component 172 (FIG. 1B) to determine a second blood pressure classifier (e.g., as part of the classifiers 170, FIG. 1B) based on a third subset from the training dataset 132 (FIG. 1B) that satisfies a third blood pressure threshold and a second subset from the training dataset 132 that satisfies a fourth blood pressure threshold. In some implementations, the third blood pressure threshold and the fourth blood pressure threshold may be distinct blood pressure values.

At block 610, method 600 may transmit the regression representations and the blood pressure classifiers to the electronic device. In some implementations, computing device 140 (FIGS. 1A and 1B) may use the communications component to transmit the regression representations 138 (FIG. 1B) and the blood pressure classifiers 170 (FIG. 1B) to the electronic device 100 (FIG. 1A).

Figure 6B:
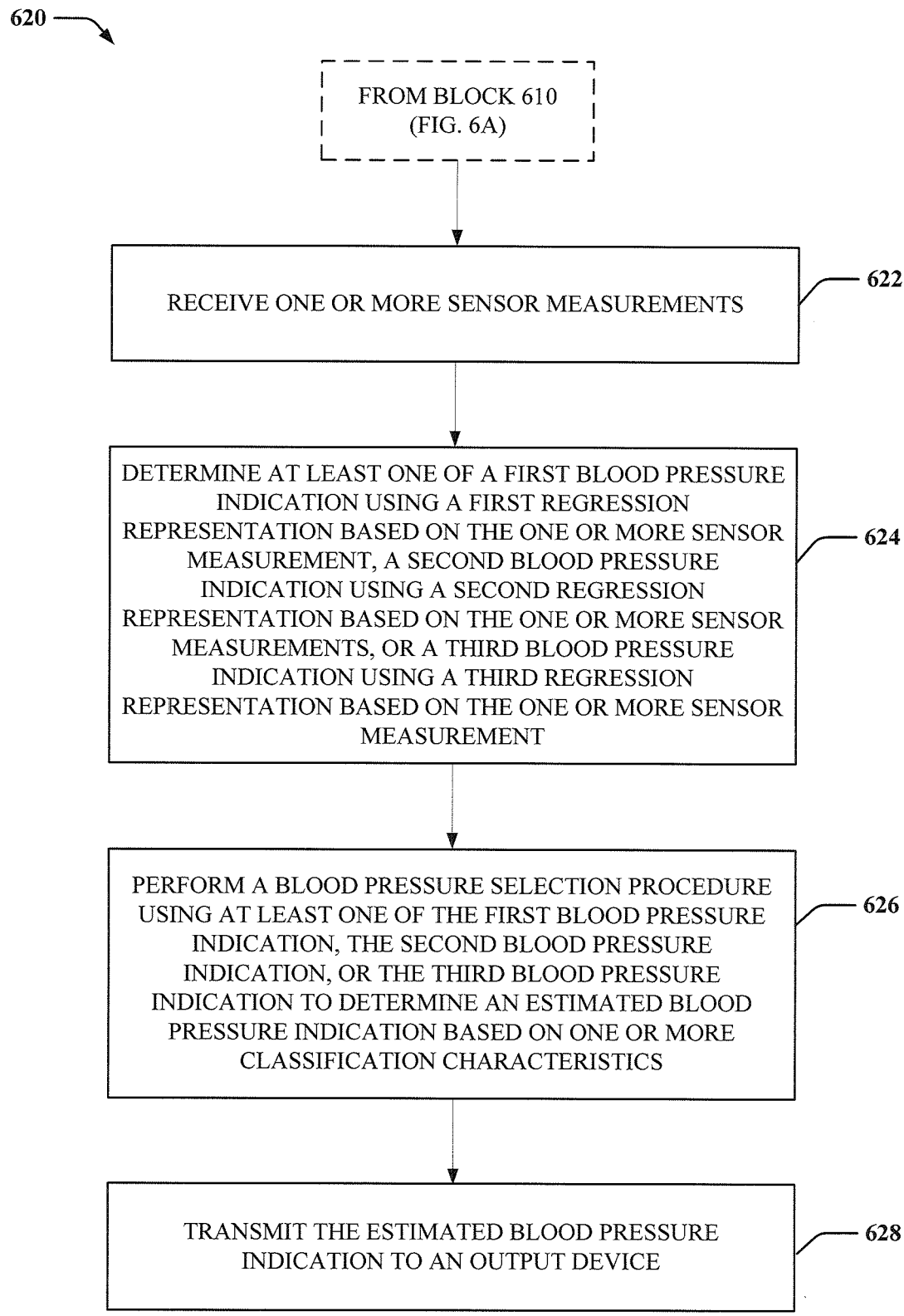
FIG. 6B is a flow chart of an example of a method of blood pressure determination in accordance with some implementations.

FIG. 6B is a flow diagram of an example of a method 620 related to blood pressure determinations in accordance with various implementations of the present disclosure. Although the operations described below are presented in a particular order and/or as being performed by an example component, it should be understood that the ordering of the actions and the components performing the actions may be varied, depending on the implementation. In some implementations, method 620 may continue from block 610 (FIG. 6A).

At block 622, method 620 may receive one or more sensor measurements. In some implementations, electronic device 100 (FIG. 1A) may execute one or more sensors 130 (FIG. 1A) including the optical emitter and sensor 134 (FIG. 1A) and/or the EKG sensor 136 (FIG. 1A) to receive one or more sensor measurements 150 (FIG. 1B). In some implementations, the one or more sensor measurements include at least one of a PPG measurement or an EKG measurement.

At block 624, method 620 may determine at least one of a first blood pressure indication using a first regression representation based on the one or more sensor measurements, a second blood pressure indication using a second regression representation based on the one or more sensor measurements, or a third blood pressure indication using a third regression representation based on the one or more sensor measurements. In some implementations, electronic device 100 (FIG. 1A) may execute blood pressure determination component 110 (FIG. 1B) to determine one or more of a first blood pressure indication 154 (FIG. 1B) using a first regression representation 152 (FIG. 1B) based on the one or more sensor measurements 150, a second blood pressure indication 160 (FIG. 1B) using a second regression representation 158 (FIG. 1B) based on the one or more sensor measurements 150, or a third blood pressure indication 164 (FIG. 1B) using a third regression representation 162 (FIG. 1B) based on the one or more sensor measurements 150.

In some implementations, although not shown, method 620 may determine at least one of an EKG RS wave segment characteristic based on the EKG measurement or a PPG area ratio value based on the PPG measurement. As such, the first blood pressure indication 154, the second blood pressure indication 160, and the third blood pressure indication 164 are determined based on at least one of the EKG RS wave segment characteristic or the PPG area ratio value.

At block 626, method 620 may perform a blood pressure selection procedure using at least one of the first blood pressure indication, the second blood pressure indication, or the third blood pressure indication to determine an estimated blood pressure indication based on one or more classification characteristics. In some implementations, electronic device 100 (FIG. 1A) may execute blood pressure determination component 110 (FIG. 1B) to perform a blood pressure selection procedure 166 (FIG. 1B) using at least one of the first blood pressure indication 154, the second blood pressure indication 160, or the third blood pressure indication 164 to determine an estimated blood pressure indication 168 (FIG. 1B) based on one or more classification characteristics (e.g., blood pressure characteristics 108, FIG. 1B).

In some implementations, the first blood pressure indication 154, the second blood pressure indication 160, and the third blood pressure indication 164 are each associated with a respective probability value.

Additionally, in some implementations, performing the blood pressure selection procedure 166 may include averaging the first blood pressure indication 154, the second blood pressure indication 160, and the third blood pressure indication 164 to form an average blood pressure indication (e.g., corresponding to the estimated blood pressure indication 168). For example, the average may be a weighted average based on a probability value of each blood pressure indication (e.g., the higher the probability value, the higher the weight value).

In some implementations, performing the blood pressure selection procedure 166 may include selecting one of the first blood pressure indication 154, the second blood pressure indication 160, or the third blood pressure indication 164 having a highest probability value. Moreover, for example, the first blood pressure indication 154, the second blood pressure indication 160, and the third blood pressure indication 164 each may be associated with a respective blood pressure class indicating a range of distinct blood pressure values.

Further, in some implementations, although not shown, method 620 may determine at least one of an average heartrate for a defined time duration based on one or both of the PPG measurement or the EKG measurement, an EKG QR width characteristic and an EKG RS width characteristic based on the EKG measurement, a normalized maximum gradient value of the PPG measurement, or a PPG area ratio value based on the PPG measurement. As such, the one or more classification characteristics (e.g., blood pressure characteristics 108) may correspond to at least one of the average heartrate for the defined time duration, the EKG QR width characteristic and the EKG RS width characteristic, the normalized maximum gradient value, or the PPG area ratio value.

At block 628, method 620 may transmit the estimated blood pressure indication to an output device. In some implementations, electronic device 100 (FIG. 1A) may execute display 112 (FIG. 1A) to output the estimated blood pressure indication 168 (FIG. 1B).

Figure 7:
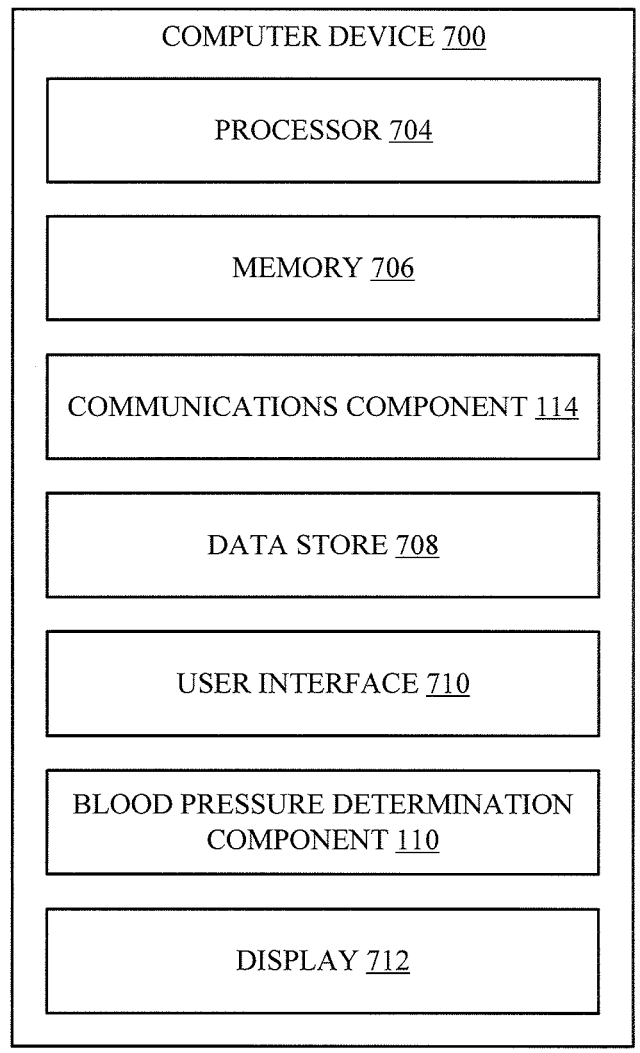
FIG. 7 is a schematic block diagram of an example electronic device in accordance with some implementations.

Referring now to FIG. 7, an example computer device 700 includes additional component details as compared to FIGS. 1A and 1B. Computer device 700 may be the same as or similar to or another version of electronic device 100 (FIG. 1A). In one implementation, computer device 700 may include processor 704 for carrying out processing functions associated with one or more of components and functions described herein. Processor 704 can include a single or multiple set of processors or multi-core processors. Moreover, processor 704 can be implemented as an integrated processing system and/or a distributed processing system.

Computer device 700 may further include memory 706, such as for storing local versions of applications being executed by processor 704. Memory 706 can include a type of memory usable by a computer, such as random access memory (RAM), read only memory (ROM), tapes, magnetic discs, optical discs, volatile memory, non-volatile memory, and any combination thereof. Additionally, processor 704 and memory 706 may include and execute blood pressure determination component (FIGS. 1A and 1B).

Further, computer device 102 may include a communications component 114 that provides for establishing and maintaining communications with one or more parties utilizing hardware, software, and services as described herein. Communications component 114 may carry communications between components on computer device 700, as well as between computer device 700 and external devices, such as devices located across a communications network and/or devices serially or locally connected to computer device 700. For example, communications component 114 may include one or more buses, and may further include transmit chain components and receive chain components associated with a transmitter and receiver, respectively, operable for interfacing with external devices.

Additionally, computer device 700 may include a data store 708, which can be any suitable combination of hardware and/or software, that provides for mass storage of information, databases, and programs employed in connection with implementations described herein. For example, data store 708 may be a data repository for blood pressure characteristics 108 (FIG. 1A) and regression representations 138 (FIG. 1A). In some implementations, computer device 700 may also include display 712 for displaying content.

Computer device 700 may also include a user interface component 710 operable to receive inputs from a user of computer device 700 and further operable to generate outputs for presentation to the user. User interface component 710 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, user interface component 710 may include one or more output devices, including but not limited to a display, a speaker, a haptic feedback mechanism, a printer, any other mechanism capable of presenting an output to a user, or any combination thereof.

As used in this application, the terms "component," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computer device and the computer device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Furthermore, various implementations are described herein in connection with a device (e.g., computer device 102 and/or trusted computer device 106), which can be a wired device or a wireless device. A wireless device may be a wearable electronic device, a cellular telephone, a satellite phone, a cordless telephone, a Session Initiation Protocol (SIP) phone, a wireless local loop (WLL) station, a personal digital assistant (PDA), a handheld device having wireless connection capability, a computer device, or other processing devices connected to a wireless modem.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Various implementations or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

The various illustrative logics, logical blocks, and actions of methods described in connection with the embodiments disclosed herein may be implemented or performed with a specially-programmed one of a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computer devices, e.g., a combination of a DSP and a microprocessor, a plurality of microprocessors, one or more microprocessors in conjunction with a DSP core, or any other such configuration. Additionally, at least one processor may comprise one or more components operable to perform one or more of the steps and/or actions described above.

Further, the steps and/or actions of a method or algorithm described in connection with the implementations disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD- ROM, or any other form of storage medium known in the art. An exemplary storage medium may be coupled to the processor, such that the processor can read information from, and write information to, the storage medium. In the alternative, the storage medium may be integral to the processor. Further, in some implementations, the processor and the storage medium may reside in an ASIC. Additionally, the ASIC may reside in a user terminal. In the alternative, the processor and the storage medium may reside as discrete components in a user terminal. Additionally, in some implementations, the steps and/or actions of a method or algorithm may reside as one or any combination or set of codes and/or instructions on a machine readable medium and/or computer readable medium, which may be incorporated into a computer program product.

In one or more implementations, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

While implementations of the present disclosure have been described in connection with examples thereof, it will be understood by those skilled in the art that variations and modifications of the implementations described above may be made without departing from the scope hereof. Other implementations will be apparent to those skilled in the art from a consideration of the specification or from a practice in accordance with implementations disclosed herein.

What is claimed is:

1. A method of blood pressure monitoring, comprising:
  receiving at least one of a photoplethysmogram "PPG" measurement or an electrocardiography "EKG" measurement associated with a user from at least one sensor;
  determining at least one of an EKG RS wave segment characteristic based on the EKG measurement or a PPG area ratio value based on the PPG measurement;
  determining, based on at least one of the EKG RS wave segment characteristic or the PPG area ratio value, at least two of a first blood pressure indication using a first regression representation, a second blood pressure indication using a second regression representation, or a third blood pressure indication using a third regression representation;
  wherein the first regression representation is trained using a first subset of a training dataset that comprises sensor data related to the at least one sensor;
  wherein the second regression representation is trained using a second subset of the training dataset;
  wherein the third regression representation is trained using a third subset of the training dataset;
  wherein the training dataset is split into the first subset, the second subset, and the third subset based on a first blood pressure threshold, a second blood pressure threshold, and a third blood pressure threshold, respectively;
  wherein each of the first regression representation, the second regression representation, and the third regression representation determines a corresponding blood pressure indication associated with a distinct blood pressure class that indicates a range of blood pressure values;
  performing a blood pressure selection procedure using at least one of the first blood pressure indication, the second blood pressure indication, or the third blood pressure indication to determine an estimated blood pressure indication based on one or more classification characteristics; and
  transmitting the estimated blood pressure indication to an output device.

2. The method of claim 1, further comprising:
  determining at least one of:
    an average heartrate for a defined time duration based on one or both of the PPG measurement or the EKG measurement;
    an EKG QR width characteristic and an EKG RS width characteristic based on the EKG measurement; or
    a normalized maximum gradient value of the PPG measurement; and
  wherein the one or more classification characteristics correspond to at least one of the average heartrate for the defined time duration, the EKG QR width characteristic and the EKG RS width characteristic, the normalized maximum gradient value, or the PPG area ratio value.

3. The method of claim 1, wherein performing the blood pressure selection procedure includes averaging the first blood pressure indication, the second blood pressure indication, and the third blood pressure indication to form an average blood pressure indication.

4. The method of claim 1, wherein the at least one sensor includes an EKG sensor.

5. The method of claim 1, wherein the at least one sensor includes a PPG sensor.

6. The method of claim 1, wherein the method is performed at a wearable electronic device.

7. The method of claim 1, wherein the output device corresponds to a display.

8. An electronic device, comprising:
  a memory to store data and instructions;
  at least one sensor to obtain at least one of a photoplethysmogram "PPG" measurement or an electrocardiography "EKG" measurement associated with a user; and
  a processor in communication with the memory and the at least one sensor, wherein the processor is configured to:
    receive at least one of the PPG measurement or the EKG measurement from the at least one sensor;
    determine at least one of an EKG RS wave segment characteristic based on the EKG measurement or a PPG area ratio value based on the PPG measurement;
    determine, based on at least one of the EKG RS wave segment characteristic or the PPG area ratio value, at least two of a first blood pressure indication using a first regression representation, a second blood pressure indication using a second regression representation, or a third blood pressure indication using a third regression representation;
wherein the first regression representation is trained using a first subset of a training dataset that comprises sensor data related to the at least one sensor;
wherein the second regression representation is trained using a second subset of the training dataset;
wherein the third regression representation is trained using a third subset of the training dataset;
wherein the training dataset is split into the first subset, the second subset, and the third subset based on a first blood pressure threshold, a second blood pressure threshold, and a third blood pressure threshold, respectively;
wherein each of the first regression representation, the second regression representation, and the third regression representation determines a corresponding blood pressure indication associated with a distinct blood pressure class that indicates a range of blood pressure values;
perform a blood pressure selection procedure using at least one of the first blood pressure indication, the second blood pressure indication, or the third blood pressure indication to determine an estimated blood pressure indication based on one or more classification characteristics; and
transmit the estimated blood pressure indication to an output device.

9. The electronic device of claim 8,
wherein the processor is further configured to determine at least one of:
an average heartrate for a defined time duration based on one or both of the PPG measurement or the EKG measurement;
an EKG QR width characteristic and an EKG RS width characteristic based on the EKG measurement; or
a normalized maximum gradient value of the PPG measurement; and
wherein the one or more classification characteristics correspond to at least one of the average heartrate for the defined time duration, the EKG QR width characteristic and the EKG RS width characteristic, the normalized maximum gradient value, or the PPG area ratio value.

10. A non-transitory computer-readable medium storing instructions executable by an electronic device, comprising at least one instruction for causing the electronic device to:
receive at least one of a photoplethysmogram "PPG" measurement or an electrocardiography "EKG" measurement associated with a user from at least one sensor;
determine at least one of an EKG RS wave segment characteristic based on the EKG measurement or a PPG area ratio value based on the PPG measurement;
determine, based on at least one of the EKG RS wave segment characteristic or the PPG area ratio value, at least two of a first blood pressure indication using a first regression representation, a second blood pressure indication using a second regression representation, or a third blood pressure indication using a third regression representation;
wherein the first regression representation is trained using a first subset of a training dataset that comprises sensor data related to the at least one sensor;
wherein the second regression representation is trained using a second subset of the training dataset;
wherein the third regression representation is trained using a third subset of the training dataset;
wherein the training dataset is split into the first subset, the second subset, and the third subset based on a first blood pressure threshold, a second blood pressure threshold, and a third blood pressure threshold, respectively;
wherein each of the first regression representation, the second regression representation, and the third regression representation determines a corresponding blood pressure indication associated with a distinct blood pressure class that indicates a range of blood pressure values;
perform a blood pressure selection procedure using at least one of the first blood pressure indication, the second blood pressure indication, or the third blood pressure indication to determine an estimated blood pressure indication based on one or more classification characteristics; and
transmit the estimated blood pressure indication to an output device.

11. The non-transitory computer-readable medium of claim 10, wherein the at least one instruction further cause the electronic device to:
determine at least one of:
an average heartrate for a defined time duration based on one or both of the PPG measurement or the EKG measurement;
an EKG QR width characteristic and an EKG RS width characteristic based on the EKG measurement; or
a normalized maximum gradient value of the PPG measurement; and
wherein the one or more classification characteristics correspond to at least one of the average heartrate for the defined time duration, the EKG QR width characteristic and the EKG RS width characteristic, the normalized maximum gradient value, or the PPG area ratio value.

12. The electronic device of claim 8, wherein, in order to perform the blood pressure selection procedure, the processor is further configured to average the first blood pressure indication, the second blood pressure indication, and the third blood pressure indication to form an average blood pressure indication.

13. The electronic device of claim 8, wherein the at least one sensor includes an EKG sensor.

14. The electronic device of claim 8, wherein the at least one sensor includes a PPG sensor.

15. The electronic device of claim 8, wherein the electronic device comprises a wearable electronic device.

16. The electronic device of claim 8, wherein the output device corresponds to a display.

17. The non-transitory computer-readable medium of claim 10, wherein, in order to perform the blood pressure selection procedure, the at least one instruction further causes the electronic device to average the first blood pressure indication, the second blood pressure indication, and the third blood pressure indication to form an average blood pressure indication.

18. The non-transitory computer-readable medium of claim 10, wherein the at least one sensor includes an EKG sensor.

19. The non-transitory computer-readable medium of claim 10, wherein the at least one sensor includes a PPG sensor.

20. The non-transitory computer-readable medium of claim 10, wherein the electronic device comprises a wearable electronic device, wherein the output device corresponds to a display.

\* \* \* \* \*